United States Patent
Mikulla et al.

(10) Patent No.: US 7,456,232 B2
(45) Date of Patent: Nov. 25, 2008

(54) USE OF BRANCHED POLYACIDS IN DENTAL COMPOUNDS

(75) Inventors: Markus Mikulla, Andechs-Frieding (DE); Guenther Lechner, Woerthsee (DE); Klaus-Peter Stefan, Seefeld (DE); Gabriele Rackelmann, Gilching (DE); Gunther Eckhardt, Bad Duerrenberg (DE)

(73) Assignee: 3M ESPE AG, Seefeld (DE)

( * ) Notice: Subject to any disclaimer, the term of this patent is extended or adjusted under 35 U.S.C. 154(b) by 647 days.

(21) Appl. No.: 10/432,946

(22) PCT Filed: Nov. 19, 2001

(86) PCT No.: PCT/EP01/13363

§ 371 (c)(1),
(2), (4) Date: Dec. 22, 2003

(87) PCT Pub. No.: WO02/41846

PCT Pub. Date: May 30, 2002

(65) Prior Publication Data

US 2004/0254260 A1    Dec. 16, 2004

(30) Foreign Application Priority Data

Nov. 27, 2000  (DE)  ............................. 100 58 830

(51) Int. Cl.
*A61K 6/083*  (2006.01)
*C08F 290/04*  (2006.01)

(52) U.S. Cl. ................... 523/116; 523/117; 523/206; 524/504

(58) Field of Classification Search ............ 523/116, 523/117, 206
See application file for complete search history.

(56) References Cited

U.S. PATENT DOCUMENTS

| | | | |
|---|---|---|---|
| 3,066,112 A | 11/1962 | Bowen | |
| 3,347,954 A | 10/1967 | Bredereck et al. | |
| 3,541,068 A | 11/1970 | Taylor | |
| 4,095,018 A | 6/1978 | Schmitt et al. | |
| 4,174,334 A | 11/1979 | Bertenshaw et al. | |
| 4,298,738 A | 11/1981 | Lechtken et al. | |
| 4,360,605 A | 11/1982 | Schmitt et al. | |
| 4,376,835 A | 3/1983 | Schmitt et al. | |
| 4,443,587 A | 4/1984 | Schmitt et al. | |
| 4,447,520 A | 5/1984 | Henne et al. | |
| 4,522,693 A | 6/1985 | Henne et al. | |
| 4,569,954 A | 2/1986 | Wilson et al. | |
| 4,737,593 A | 4/1988 | Ellrich et al. | |
| 4,872,936 A | 10/1989 | Engelbrecht | |
| 5,141,560 A | 8/1992 | Combe et al. | |
| 5,374,336 A * | 12/1994 | Lin et al. | ......... 162/168.3 |
| 5,739,210 A * | 4/1998 | Scranton et al. | ......... 525/279 |
| 5,824,720 A | 10/1998 | Nowak et al. | |
| 6,875,801 B2 * | 4/2005 | Shendy et al. | ......... 524/5 |
| 2005/0183837 A1 * | 8/2005 | Chen et al. | ......... 162/173 |

FOREIGN PATENT DOCUMENTS

| | | |
|---|---|---|
| DE | 1 495 520 | 4/1969 |
| DE | 2 061 513 | 6/1971 |
| DE | 2 319 715 | 10/1973 |
| DE | 20 65 824 A1 | 3/1976 |
| DE | 2658538 A1 | 6/1977 |
| DE | 28 16 823 A1 | 10/1978 |
| DE | 29 29 121 A1 | 2/1981 |
| DE | 44 45 266 A1 | 6/1996 |
| DE | 195 25 033 A1 | 1/1997 |
| DE | 199 28 238 A1 | 12/2000 |
| EP | 0 007 508 A2 | 2/1980 |
| EP | 0 024 056 A2 | 2/1981 |
| EP | 0 047 902 A2 | 3/1982 |
| EP | 0 057 474 A2 | 8/1982 |
| EP | 0 059 451 A1 | 9/1982 |
| EP | 0 073 413 A2 | 3/1983 |
| EP | 0 007 508 B1 | 6/1983 |
| EP | 0 057 474 B1 | 10/1984 |
| EP | 0 047 902 B1 | 11/1984 |
| EP | 0 073 413 B1 | 12/1984 |
| EP | 0 059 451 B1 | 7/1985 |
| EP | 0 024 056 B1 | 11/1985 |
| EP | 0 184 095 A2 | 6/1986 |

(Continued)

OTHER PUBLICATIONS

"Testing of Plastic Materials Hardness Testing by means of Indentation Test," German Standards, DK 678.5/.8: 178.152.2, DIN 53 456, published by International Organization for Standardization (ISO) ISO/DIS 2039, printed in German with English Language Translation included (8 pgs. total) (Jan. 1973).

(Continued)

*Primary Examiner*—Tae H Yoon
(74) *Attorney, Agent, or Firm*—Mueting, Raasch & Gebhardt, P.A.

(57) ABSTRACT

The invention relates to dental compounds that contain at least one polyacid or at least one polyacid and at least one salt of at least one polyacid. The polyacids used have at least one branch point in the polymer structure and are water-soluble and not cross-linked and their repeat units consist to at least 80 mole % of acrylic acid segments.

19 Claims, No Drawings

FOREIGN PATENT DOCUMENTS

| | | |
|---|---|---|
| EP | 0 219 058 A2 | 4/1987 |
| EP | 0 184 095 B1 | 7/1989 |
| EP | 0 374 824 A2 | 6/1990 |
| EP | 0 374 824 A3 | 6/1990 |
| EP | 0 219 058 B1 | 6/1991 |
| EP | 0 374 824 B1 | 9/1993 |
| EP | 0 219 058 B2 | 10/1994 |
| GB | 1 316 129 | 5/1973 |
| GB | 1 520 199 | 8/1978 |
| GB | 1 576 080 | 10/1980 |
| JP | 54160752 | 12/1979 |
| JP | 3-240713 A | 10/1991 |
| JP | 4-221303 | 8/1992 |
| JP | 4-221304 | 8/1992 |
| WO | WO 98/32433 | 7/1998 |

OTHER PUBLICATIONS

A. Akar et al., "Low molecular weight poly(acrylic acid) with nitrilodi(methylene-phosphonic acid) chain ends for scale inhibition," *Die Angewandte Makromolekulare Chemie (Applied Macromolecular Chemistry and Physics)*, vol. 273, Title page, Publication page, Table of Contents, and pp. 12-14 (7 pgs. total) (Dec. 1999).

Angot et al., "Atom Transfer Radical Polymerization of Styrene Using a Novel Octafunctional Initiator: Synthesis of Well-Defined Polystyrene Stars," *Macromolecules*, vol. 31, No. 21, Title page, Publication page, Table of Contents, and pp. 7218-7225 (14 pgs. total) (Oct. 20, 1998).

Banerjee et al., "Metal-Free Carbanion salts for the Living Anionic Polymerization of Alkyl (Methyl) Acrylates," *Macromolecules*, vol. 31, No. 22, Title page, Publication page, Table of Contents, and pp. 7966-7969 (10 pgs. total) (Nov. 3, 1998).

Crisp et al., "Glass-ionomer Cement Formulations. II. The Synthesis of Novel Polycarboxylic Acids," *Journal of Dental Research*, vol. 59, No. 6, Title page, Publication page, Table of Contents, and pp. 1055-1063 (12 pgs total) (Jun. 1980).

Davis et al., "Atom Transfer Radical Polymerization of T-Butyl Acrylate," *Polymer Preprints*, vol. 40, No. 2, Title page, Publication page, Table of Contents; and pp. 430-431(5 pgs. total) (Aug. 1999).

Haddleton et al., "Atom transfer polymerisation with glucose and cholesterol derived initiators," *New Journal of Chemistry*, vol. 23, No. 5, Title page, Publication page, Table of Contents, and pp. 477-479 (9 pgs. total)(May 1999).

Heise et al., "Novel Starlike Poly(methyl methacrylate)s by Controlled Dendritic Free Radical Initiation," *Macromolecules*, vol. 32, No. 1, Title page, Publication page, Table of Contents, and pp. 231-234 (9 pgs. total) (Jan. 12, 1999).

Heise et al., "Star-Like Amphiphilic Block Copolymers—Models for Unimolecular Micelles and Nanoreactors," *Polymer Preprints*, vol. 40, No. 1, Title page, Publication page, Table of Contents, and pp. 452-453 (5 pgs. total) (Mar. 1999).

International Standard, ISO 4049, "Dentistry—Polymer-based filling, restorative and luting materials," Title page, Publication page, Table of Contents, Forward page, Introduction page, and pp. 1-27 (34 pp. total) (Jul. 15, 2000).

International Standard, ISO 9917, "Dental water-based cements," Title page, Publication page (with forward), Introduction, and pp. 1-13 (18 pp. total) Dec. 15, 1991).

Matyjaszewski et al., "Synthesis and Characterization of Star Polymers with Varying Arm Number, Length, and Composition from Organic and Hybrid Inorganic/Organic Multifunctional Initiators," *Macromolecules*, vol. 32, No. 20, Title page, Publication page, Table of Contents, and pp. 6526-6535 (16 pgs. total) (Oct. 5, 1999).

Pugh et al., "Miscibility of SCLCPS with Different Architectures," *Polymer Preprints*, vol. 40, No. 2, Title page, Publication page, Table of Contents, and pp. 108-109 (5 pgs. total) (Aug. 1999).

D.C. Smith, "A New Dental Cement," *British Dental Journal*, vol. 125, No. 9, Title page, Publication page, Table of Contents, and pp. 381-384 (8 pgs. total) (Nov. 5, 1968).

Cook, W. D., "Setting of dental polyelectrolyte cements - viscosity studies of model systems," *Journal of Biomedical Materials Research*, 1983;17:283-291.

Ouyang et al., "New Method for Monitoring the Reaction of Glass Ionomer Cements: A Spectroscopic Study of the Effects of Polyacid Structure on the Decomposition of Calcium Aluminosilicate Glasses," *Applied Spectroscopy*, 1999;53(3):297-301.

* cited by examiner

USE OF BRANCHED POLYACIDS IN DENTAL COMPOUNDS

The present application is a U.S. National Stage Application of PCT/EP01/13363, filed 19 Nov. 2001. The application also claims the benefit under 35 U.S.C. 119 of foreign application no. DE 100 58 830.1, filed 27 Nov. 2000.

The invention relates to the use of branched, non-crosslinked, water-soluble polyacids in dental products, in particular in dental cements, such as zinc polycarboxylate cements, glass ionomer cements (GICs), resin-modified glass ionomer cements (RM-GICs) and compomers, insofar as they can be formulated with aqueous polyacid solutions.

Polyacids have been used for a long time in the formulation of curable dental materials. For example, polyacrylic acid was used as ground substance in zinc polycarboxylate cements (D. C. Smith, Br. Dent. J., 125 (1968), 381-384) or also in glass ionomer cements (ASPA I, Wilson and Kent, 1969; DE 20 615 13 A1).

While zinc polycarboxylate cements to this day are based on polyacrylic acid, the glass ionomer cements were developed further with regard to the chemical composition of the polyacid.

For example, copolymeric acids of acrylic acid and itaconic acid for use in glass ionomer cements are known from S. Crisp, B. E. Kent, B. G. Lewis, A. J. Ferner and A. D. Wilson, J. Dent, Res., 59, (1980), 1055-1063. In addition, glass ionomer cements based on a copolymer of acrylic acid and maleic acid are disclosed in EP 0 024 056 A1.

Highly concentrated, for example approx. 30 to 50%, aqueous solutions of unbranched polyacids are usually used in dental materials, for example in polyelectrolyte cements and especially in zinc polycarboxylate cements and glass ionomer cements.

Highly branched, partially crosslinked polyacids for use in dental products are disclosed in JP 4-221 303 and JP 4-221 304. However, these polyacids are no longer sufficiently soluble in water to be completely available for the setting reaction in dental products, so that unreacted defects arise which weaken the set material.

The overall proportion of polyacid in dental cements generally has to be chosen to be as high as possible in order to achieve the maximum strengths of the cured cement. At the same time, care must be taken that the system exhibits a manageable viscosity on mixing and applying. This is important in particular in preparations which will be expelled into mixing capsules, since the mixed material has to flow through an outlet nozzle.

The following approaches for optimizing are known in this connection:

1. In GICs, a proportion of the polyacid used is mixed into the powder. However, the proportion in the powder is limited, in particular in reinforced glass ionomer filling cements, since only a little polyacid from the powder can be dissolved on mixing with GIC liquid in the short processing time necessary when used in a dental surgery. Undissolved amounts of polyacid from the powder act in the cement as defects and consequently lead to a weakening of the material.

2. A reduction in the overall content of polyacid in dental cements is generally, and especially in reinforced GICs, accompanied by an obvious deterioration in the mechanical strength of the cured cement.

The polyacid most frequently employed in dental products is unbranched polyacrylic acid. However, in concentrated aqueous solution, this polyacid has a tendency to undergo irreversible gelling. Such gelled polyacrylic acid solutions cannot be employed for use in dental cements. Methanol has been added to the polyacrylic acid solutions to counter this effect, but methanol, on the one hand, is poisonous and, on the other hand, leads to discoloring of the cement in the oral environment.

3. An additional approach to this solution consisted in using copolymers of acrylic acid and itaconic acid or maleic acid for dental cement liquids. The gelling could thereby be prevented. However, this resulted in some undesired properties for the dental cements prepared from them, such as deficient self-adhesion of the cements to the dental hard substance and, in particular in reinforced glass ionomer cements in filling therapy, 10 to 20% lower bending strengths and because of that reduced long-term performance.

That is why, for use in dental products, there exists a demand for polyacids which are miscible with aqueous solutions, which show no tendency to gel and which lead to excellent physical properties of the cured dental products.

Surprisingly, it has now been found that polyacids in which at least 80 mol % of the repeat units are formed from acrylic acid segments and which simultaneously exhibit a branched but noncrosslinked polymer structure do not gel, prevent the disadvantages known in the state of the art and are for this reason outstandingly suitable for use in dental products.

The terms "including" and "comprising" introduce, in the context of this application, an enumeration which is not comprehensive. The term "one" is equivalent to the statement of "at least one".

The dental materials are normally curable materials, i.e. materials which in accordance with the requirements change in a period of time of 30 sec to 30 min, preferably of 2 min to 10 min, from a viscous to a nonviscous condition. The curing reaction can, for example, be brought about by a cement reaction, a crosslinking reaction and/or a polymerization reaction.

A viscous condition, in contrast to a nonviscous condition, in the above mearing then exists if the material can be processed or applied with application devices familiar to dentists, such as a spatula, syringe or mixing capsule.

The term "gelling" should be understood, within the meaning of this invention, as meaning a process in which the aqueous solution of a polyacid changes from a flowable to a rigid form, this operation being irreversible.

The term "polyacids" should be understood, within the context of this invention, as meaning polymers and copolymers which exhibit more than three acid groups per polymer molecule and optionally other additional functional groups.

The term "acid groups" is to be understood as meaning in particular carboxylic acid groups, phosphonic acid groups, phosphoric acid groups or sulfonic acid groups.

The term "branched polyacids" is to be understood as meaning polyacids which comprise at least one branching point in the polymer structure. Examples of branched polymer structures are star polymers, comb polymers, graft polymers, long-chain-branched polymers, short-chain-branched polymers, hyperbranched polymers or dendrimers.

A side group which sticks out from a polymer chain is not a branching point according to the invention. Crosslinkages produced by complexing reactions are also not branchings within the meaning of the invention. Repeat units are always connected from a branching point. According to the invention, the term "branching point" is to be understood as meaning a position in the polymer backbone from which, covalently bonded, at least two, preferably three, polymer residues start out, these comprising at least three repeat units.

A polyacid is then water-soluble within the meaning of the invention if an aqueous, completely clear, solution comprising at least one percent by weight of a polyacid can be prepared. In contrast thereto, crosslinked polymers are, as is known, generally insoluble under standard conditions in the solvents current in the dental field.

Star polymers or comb polymers are preferred for the invention, particularly preferably star polymers.

In star polymers, at least three in themselves unbranched polymer chains, preferably with at least three repeat units, are combined together via a common branching point. A branching point can be a polyvalent atom or can have a low-molecular-weight molecular structure, such as a benzene ring or a cyclohexane ring.

In comb polymers, at least two polymer chains are connected laterally to a common main polymer chain which in itself is unbranched.

Dental products according to the invention are accordingly those including at least one polyacid, optionally together with at least one salt of at least one polyacid, in which the polyacids used have at least one, preferably one, branching point in the polymer structure, are water-soluble and noncrosslinked and, with regard to the repeat units, comprise at least 80 mol %, preferably at least 90 mol %, particularly preferably at least 95 mol %, and very particularly preferably 100 mol % acrylic acid segments.

The term "repeat units" is to be understood as meaning not the structural units of the branching points but exclusively the segments which repeat themselves of the preferably linear polymer chains starting out from the branching points. In copolymeric acids, the different repeat units are usually arranged randomly.

The molecular weight distribution Mw/Mn of the polyacids is in each case, according to the method of preparation, usually between 1.0 and 10.0, preferably in the range from 1.5 to 6.0; however, higher values can also be accepted.

The term "Mw" is to be understood, within the meaning of this application, as meaning the weight-average molecular weight determined by means of aqueous gel permeation chromatography (GPC), for which applies:

$$Mw = \frac{\sum_i n_i M_i^2}{\sum_i n_i M_i}$$

in which $n_i$=number of the polymer chains and $M_i$=molar mass of the polymer chain.

The term "Mn" is to be understood, within the meaning of this application, as meaning the number-average molecular weight determined by means of aqueous GPC, for which applies:

$$Mn = \frac{\sum_i n_i M_i}{\sum_i n_i} = \frac{\sum_i n_i M_i}{n}$$

in which n=total number of the polymer chains in a sample.

An additional advantage of the use according to the invention of branched polyacids is the high bending strengths which can be obtained. It is possible, with glass ionomer filling cements, for example, to obtain bending strengths which are shifted to the high level of the known systems based on linear polyacrylic acid.

Curable dental materials or cements can be prepared with the polyacids described, which dental materials or cements, for example, exhibit via a compressive strength ranging from 200 to 260 MPa (measured according to ISO 9917), a bending strength ranging from 30 to 50 MPa (measured analogously to ISO 4049 with test specimens 12 mm long) and/or a surface hardness ranging from 350 to 510 MPa (measured according to DIN 53456).

A further advantage of the dental products according to the invention comprising branched polyacids is that distinctly reduced viscosities are found in a concentrated aqueous solution of the branched polyacids, which leads to a simplified miscibility of powder and liquid.

In addition, the dental products according to the invention have the advantage that no toxic or other undesired constituents or additives are present.

The branched polyacids present in the dental products according to the invention are accessible in principle according to different methods of preparation.

"Arm-first" and "core-first" synthetic principles known for star polymers (K. Matyjaszewski et al., Macromolecules, 1999, 32, p. 6526) are valid in principle for comb polymers as well.

1. Star and comb polymeric acids can be prepared according to the "arm-first method" from linear polyacids or their derivatives which can be converted to polyacids, which have a functional chain end, by reactive coupling to a polyfunctional low-molecular-weight, for example cyclic, compound or oligomeric, for example macrocyclic or linear polymeric, compound. Mention may be made, as general examples, of:

a) preparation of polyacrylic acid with an amino end group, for example by free radical polymerization in the presence of an amino-functional transfer reagent (A. Akar, N. Öz, Angew. Makromol, Chem., 273, 1999, 12-14) and subsequent reaction, for example with poly-functional carbonyl chlorides or carboxylic anhydrides, such as benzenetricarbonyl trichloride, butanetetracarbonyl tetrachloride, oligomeric maleic anhydride, acryloyl chloride polymers, such as poly(acrylic acid-co-acryloyl chloride), polyfunctional benzyl halides, such as 1,2,4,5-tetrakis(bromomethyl)benzene, hexakis(bromomethyl)benzene, with tetra(bromomethyl)pentaerythritol or other low-molecular-weight oligomeric or polymeric coupling reagents. 1,4-Dioxane is frequently particularly suitable for carrying out the coupling reaction since it constitutes a good solvent for polyacrylic acid.

b) Polyacrylic acid derivatives, such as poly(tert-butyl acrylate), with end group functionalizing can also be used as functional polyacid derivatives, in which derivatives alcohol or thiol groups are, for example, also possible as end groups, in addition to the preferred primary or secondary amino groups. After a coupling of these polymers analogous to 1.a), the tert-butyl ester groups have to be selectively cleaved. This can occur, for example, by heating the polymer in a dioxane solution with hydrochloric acid (K. A. Davis et al., Polymer Prepr., 2/1999, 430).

c) Poly(butyl acrylate) prepared by anionic polymerization (P. Banerjee and A. M. Mayes, Macromolecules, 1998, 31, 7966) can also be used as polyacrylic acid derivative and is reacted as anionic entity according to 1.a) with a coupling reagent. The butyl ester groups are subsequently removed according to conventional methods, for example by acid or alkaline hydrolysis in an aqueous/organic medium, such as a dioxane/water mixture.

2. Star and comb polymeric acids can be prepared according to the "core-first method" by grafting acid monomers or their derivatives which can be converted to acid segments to polyfunctional low-molecular-weight, cyclic, oligomeric, macrocyclic or linear polymeric initiators according to a living polymerization mechanism, preferably an anionic or living free-radical mechanism. The living polymerization mechanism in this connection avoids the formation of more highly branched or crosslinked polymers. Atom Transfer Polymerization (ATRP) can preferably be applied in living free-radical polymerization.

a) Polyfunctional initiators for the preparation of acrylate star polymers are described, for example, in C. Pugh et al., Polymer Prepr., 2/1999, 108; D. M. Haddleton et al., New J. Chem., 1999, 23, 477; Heise et al., Polymer Prepr., 1/1999, 452; A. Heise et al., Macromolecules, 1999, 32, 231; S. Angot et al., Macromolecules, 1998, 31, 7218. The cleavage of the polyacrylate ester groups subsequently necessary can be carried out according to the usual methods.

b) Polyfunctional initiators for the synthesis of acrylate comb polymers can, for example, be copolymers or oligomers of acrylates and 4-chloromethylstyrene, the benzylic chloride groups being suitable as ATRP initiator for acrylates. After the ATRP, the acrylate groups in the main chain and in the side chains can be cleaved according to the usual methods to give acrylic acid segments.

In addition to the acrylic acid segments, additional acid repeat units or also other functional or nonfunctional repeat units and groups can be present in the polyacids in a total of 0.1 to 20 mol %, preferably 0.1 to 10 mol %, particularly preferably 0.1 to 5 mol %.

The additional acid repeat units can, for example, be produced from the copolymerization of acrylic acid with methacrylic acid, maleic acid, maleic anhydride, fumaric acid, itaconic acid, itaconic anhydride, glutaconic acid, citridic acid, citraconic acid, methaconic acid, tiglic acid, crotonic acid, muconic acid, isocrotonic acid, 3-butenoic acid, cinnamic acid, styrenecarboxylic acid, vinylphthalic acid, abietinic acid, styrenesulfonic acid, styrenephosphonic acid, 1-phenylvinylphosphonic acid, vinylphosphonic acid, vinylidenediphosphonic acid, vinylsulfonic acid, vinyl phosphate or other monomers with acid functional groups and substituted derivatives thereof, especially esters or amides or imides of the acids mentioned with up to 10 carbon atoms in the alkoxide residue or amine residue or imine residue, for example maleimide, N-methylmaleimide, N-ethylmaleimide, acrylamide, N-methylacrylamide, N,N-dimethylacrylamide, N-ethylacrylamide, methyl acrylate, ethyl acrylate, n-propyl acrylate, isopropyl acrylate, n-butyl acrylate, isobutyl acrylate or tert-butyl acrylate.

Examples of other functional repeat units are structural segments produced from vinyl acetate, vinyl ethers, for example vinyl methyl ether, vinyl alcohol, butadiene, isoprene, styrene, vinyl chloride, vinylidene dichloride, vinyl fluoride or vinylidene difluoride.

Examples of nonfunctional repeat units are structural units produced from ethylene, propylene, tetramethylene, 1-butene, 1-pentene or 1-hexene.

The polyacids can, according to the field of application, be used as liquid or, if appropriate, additionally as solid, for example obtained through freeze drying or spray drying.

The polyacids usually exhibit a molecular weight Mw ranging from 1000 to 1 000 000, preferably ranging from 10 000 to 500 000.

The polyacids are preferably used as aqueous solutions with 1 to 70% by weight, preferably 20 to 60% by weight, particularly preferably 30 to 50% by weight, at a temperature of 22° C.

The cations of the salts of the polyacids which can be used according to the invention are taken from the group: alkali metal elements, alkaline earth metal elements, zinc, aluminum, scandium, yttrium and lanthanum. Na, Ca and Al salts are preferred in this connection.

Preferred dental materials in the context of this invention are either formulated with a single component, such as compomers, or with two or more components, such as carboxylate cements, glass ionomer cements and resin-modified glass ionomer cements, in which the liquid components are stored separately from the solid components and are mixed immediately before application.

At the same polyacid concentration, as a result of a reduced solution viscosity of the polyacids according to the invention, higher P/L ratios can be set and still well managed (up to approximately 30% higher) than in the polyacids known in the state of the art. This regularly also results in improved material strengths (up to approximately 20% improved values in compressive strength and bending strength).

Powder/liquid ratios which can be used range from 0.7 to 6, preferably from 1 to 5, particularly preferably from 1.5 to 3.5.

Particular preference is given to cements which, in the case of glass ionomer cements, for example, can include the following constituents:

(A) 1 to 60% by weight, preferably 5 to 40% by weight, particularly preferably 10 to 30% by weight, of polyacids, optionally together with at least one salt of at least one polyacid, in which the polyacids used have at least one, preferably one, branching point in the polymer structure, are water-soluble and noncrosslinked and, with regard to the repeat units, comprise at least 80 mol %, preferably 90 mol %, particularly preferably 95 mol % and very particularly preferably 100 mol % acrylic acid segments;

(B) 35 to 80% by weight, preferably 50 to 70% by weight, of fillers;

(C) 0 to 20% by weight, preferably 1 to 10% by weight, of additives and auxiliaries;

(D) 5 to 40% by weight, preferably 9 to 30% by weight, of water.

The term "fillers" of the component (B) is to be understood as mainly reactive or nonreactive solids.

Suitable examples are reactive fluoroaluminosilicate glasses from DE 20 61 513 A, DE 20 65 824 A, or reactive glasses which, on the surface, in comparison with the average composition, are depleted in calcium ions, as described in DE 29 29 121 A.

The last-named glasses are especially preferred and can exhibit the following composition:

| Constituent | Calculated as | % by weight |
| --- | --- | --- |
| Si | $SiO_2$ | 20 to 60 |
| Al | $Al_2O_3$ | 10 to 50 |
| Ca | CaO | 1 to 40 |
| F | F | 1 to 40 |
| Na | $Na_2O$ | 0 to 10 |
| P | $P_2O_5$ | 0 to 10 | and in addition a total of 0 to 20% by weight, calculated as oxides, of B, Bi, Zn, Mg, Sn, Ti, Zr, La or other trivalent lanthanides, K, W, Ge, and other additives, which do not impair the properties and are physiologically completely harmless.

In addition to the reactive glasses described above, inert fillers, such as quartz, can be used.

The term "component (C)" is to be understood as, for example, additives for accelerating and improving the curing, as are known from DE 2 319 715 A. Preferably, chelating agents in the form of low molecular weight acid molecules, such as tartaric acid, are added.

Coloring pigments and other auxiliaries usual in the field of glass ionomer cements, for example for improving the miscibility, are also to be understood under "component (C)".

Apart from their use in conventional glass ionomer cements, the polyacids described here are also suitable for use in carboxylate cements.

In this connection, the compositions include, for example, the following constituents:

(A) 1 to 60% by weight, preferably 5 to 40% by weight, of polyacids, particularly preferably 10 to 30% by weight, optionally together with at least one salt of at least one polyacid, in which the polyacids used have at least one, preferably one, branching point in the polymer structure, are water-soluble and noncrosslinked and, with regard to the repeat units, comprise at least 80 mol %, preferably 90 mol %, particularly preferably 95 mol % and very particularly preferably 100 mol % acrylic acid segments;
(C) 0 to 20% by weight, preferably 1 to 10% by weight, of additives and auxiliaries;
(D) 10 to 40% by weight, preferably 15 to 30% by weight, of water;
(E) 30 to 80% by weight, preferably 44 to 70% by weight, of zinc oxide.

Compomers or resin-modified glass ionomer cements comprising the polyacids described here include, for example, the following components:

(A) 1 to 76% by weight, preferably 2 to 69.9% by weight, particularly preferably 10 to 40% by weight, of polyacids, optionally together with at least one salt of at least one polyacid, in which the polyacids used have at least one, preferably one, branching point in the polymer structure, are water-soluble and noncrosslinked and, with regard to the repeat units, comprise at least 80 mol %, preferably 90 mol %, particularly preferably 95 mol % and very particularly preferably 100 mol % acrylic acid segments;
(D) 5 to 40% by weight, preferably 5 to 35% by weight, of water;
(F) 8.9 to 70% by weight, preferably 10 to 60% by weight, of one or more radically polymerizable monomers;
(G) 10 to 90% by weight, preferably 15 to 87.9% by weight, of fillers;
(H) 0.1 to 5% by weight, preferably 0.5 to 3% by weight, of initiators and optionally activators;
(I) 0 to 30% by weight, preferably 0.1 to 20% by weight, of additives, optionally pigments, thixotropic auxiliaries, plasticizers.

Mono-, di- or polyfunctional ethylenically unsaturated compounds, preferably based on acrylate and/or methacrylate, are used as component (F). These can comprise both monomeric and polymolecular oligomeric or polymeric acrylates. In addition, they can be used in the formulations alone or as mixtures.

Suitable monomers are, for example, the acrylic and methacrylic esters of mono-, di- or polyfunctional alcohols. The following are mentioned as examples: 2-hydroxyethyl (meth) acrylate, methyl (meth)acrylate, isobutyl (meth)acrylate, ethylene glycol di(meth)acrylate, triethylene glycol di(meth) acrylate (TEGDMA), hexanediol di(meth)acrylate, dodecanediol di(meth)acrylate and trimethylolpropane tri (meth)acrylate.

Others which can advantageously be used are bisphenol A di(meth)acrylate and the ethoxylated or propoxylated di(meth)acrylates derived therefrom. In addition, the monomers described in U.S. Pat. No. 3,066,112, based on bisphenol A (meth)acrylate and glycidyl (meth)acrylate or their derivatives arising from addition of isocyanates, are suitable.

The diacrylic and dimethacrylic esters of bis(hydroxymethyl)tricyclo $[5.2.1.0^{2,6}]$decane mentioned in DE 28 16 823 C and the diacrylic and dimethacrylic esters of the compounds of bis(hydroxymethyl)tricyclo $[5.2.1.0^{2,6}]$decane extended with 1 to 3 ethylene oxide and/or propylene oxide units are also especially suitable.

Urethane (meth)acrylates, such as 7,7,9-trimethyl-4,13-dioxo-5,12-diazahexadecane-1,16-dioxy dimethacrylate (UDMA), can also be a constituent of this component.

Fillers according to component (G) can be inorganic fillers, for example quartz, glass powder, water-insoluble fluorides, such as $CaF_2$, silica gels and silicic acid, especially pyrogenic silica, and their granulates. Cristobalite, calcium silicate, zirconium silicate, zeolites, including molecular sieves, metal oxide powders, such as aluminum or zinc oxides or their mixed oxides, barium sulfate, yttrium fluoride or calcium carbonate can also be used as fillers.

Fluoride-releasing fillers, for example complex inorganic fluorides of the general formula $A_nMF_m$, as described in DE 44 45 266 A, can also be used or added. A represents a mono- or polyvalent cation, M represents a metal from the main group or subgroup III, IV or V, n represents an integer from 1 to 3 and m represents an integer from 4 to 6.

Organic fillers can also be a constituent of this component.

Those mentioned by way of example are conventional pearl-shaped polymers and copolymers based on methyl methacrylate, which, for example, are available from Rohm under the name "Plexidon" or "Plex".

For improved incorporation in the polymer matrix, it can be advantageous to render hydrophobic, using a silane, the fillers mentioned and optionally additives opaque to X-rays. The amount of the silane used usually amounts to 0.5 to 10% by weight, with reference to inorganic fillers, preferably 1 to 6% by weight, very particularly preferably 2 to 5% by weight, with reference to inorganic fillers. Normal hydrophobing agents are silanes, for example trimethoxymethacryloyl-oxypropylsilane. The maximum mean particle size of the inorganic fillers preferably amounts to 15 µm, in particular 8 µm. Fillers with a mean particle size of <3 µm are very particularly preferably used.

The term "initiators" according to component (H) is to be understood as initiator systems which bring about the radical polymerization of monomers, for example photoinitiators and/or what are known as redox initiator systems and/or thermal initiators.

Examples of suitable photoinitiators are α-diketones, such as camphorquinone, in conjunction with secondary and tertiary amines, or mono- and bisacylphosphine oxides, such as 2,4,6-trimethylbenzoyldiphenylphosphine oxide and bis(2,6-dichlorobenzoyl)(4-n-propylphenyl)phosphine oxide. However, other compounds of this type, as are described in EP 0 073 413 A, EP 0 007 508 A, EP 0 047 902 A, EP 0 057 474 A and EP 0 184 095 A, are also suitable.

Organic peroxide compounds together with "activators" are suitable as redox initiator systems. Compounds such as lauroyl peroxide, benzoyl peroxide, p-chlorobenzoyl peroxide and p-methylbenzoyl peroxide are suitable in particular as organic peroxide compounds.

Tertiary aromatic amines, such as the N,N-bis(hydroxyalkyl)-3,5-xylidines known from U.S. Pat. No. 3,541,068, and the N,N-bis(hydroxyalkyl)-3,5-di(tert-butyl)anilines known from DE 26 58 530 A, especially N,N-bis(β-hydroxybutyl)-3,5-di(tert-butyl)aniline, and N,N-bis(hydroxyalkyl)-3,4,5-trimethylanilines, for example, are suitable as activators.

Highly suitable activators are also the barbituric acids and barbituric acid derivatives described in DE 14 95 520 C and the malonyl sulfamides described in EP 0 059 451 A. Preferred malonyl sulfamides are 2,6-dimethyl-4-isobutylmalonyl sulfamide, 2,6-diisobutyl-4-propylmalonyl sulfamide, 2,6-dibutyl-4-propylmalonyl sulfamide, 2,6-dimethyl-4-ethylmalonyl sulfamide and 2,6-dioctyl-4-isobutylmalonyl sulfamide.

For further acceleration, the polymerization is in this connection preferably carried out in the presence of heavy metal compounds and ionogenic halogen or pseudo-halogen. Copper is especially suitable as heavy metal and the chloride ion is especially suitable as halide. The heavy metal is suitably used in the form of soluble organic compounds. Likewise, the halide and pseudohalide ions are suitably used in the form of soluble salts. Examples which may be mentioned are the soluble amine hydrochlorides and quaternary ammonium chloride compounds.

If the dental materials according to the invention comprise a redox initiator system formed from organic peroxide and activator, peroxide and activator are then preferably present in parts of the dental material according to the invention which are spatially separate from one another, and they are homogeneously mixed with one another only immediately before use. If organic peroxide, copper compound, halide and malonyl sulfamide and/or barbituric acid are present side by side, then it is particularly sensible for the organic peroxide, malonyl sulfamide and/or barbituric acid and the copper compound/halide combination to be present in three constituents spatially separate from one another. For example, the copper compound/halide combination, polymerizable monomers and fillers can be kneaded to a paste and the other components can be kneaded to two separate pastes in the above-described way in each case with a small amount of fillers or in particular thixotropic auxiliaries, such as silanized silicic acid, and a plasticizer, for example phthalate. On the other hand, the polymerizable monomers can also be present together with organic peroxide and fillers. Alternatively, organic peroxide, copper compound, halide and malonyl sulfamide and/or barbituric acid can also be split up according to DE 199 28 238 A.

Soluble organic polymers can be used as representatives of component (I), for example for increasing the flexibility of the materials. Poly(vinyl acetate) and the copolymers based on vinyl chloride/vinyl acetate, vinyl chloride/vinyl isobutyl ether and vinyl acetate/maleic acid dibutyl ether, for example, are suitable. Dibutyl, dioctyl and dinonyl phthalates or adipates and polymolecular polyphthalic and adipic esters, for example, are highly suitable as additional plasticizers. Modified layered silicates (bentonites) or organic modifying agents, for example based on hydrogenated castor oils, can also be used, in addition to pyrogenic silicic acids, as thixotropic auxiliaries. Furthermore, inhibitors, as are described in EP 0 374 824 A as component (d), can be included in the formulations as additives.

Likewise inventive are containers comprising dental products including at least one polyacid, optionally together with at least one salt of at least one polyacid, in which the polyacid used has at least one branching point in the polymer structure, is water-soluble and noncrosslinked and, with regard to the repeat units, consists of at least 80 mol % acrylic acid segments. Such containers can, for example, be capsules, tubes, including screw-cap tubes, application syringes, application tips, cannulas, sachets, blister packs, cartons or glass containers. All containers in which several components can be stored separately from one another are suitable in principle, whereby the term "separate storage" should be understood as also meaning the physical separation of the constituents via the different states of matter.

The invention is subsequently illustrated by examples, without it being limited in any way thereby.

The determination of the molar mass distribution was carried out in this connection via aqueous gel permeation chromatrography (GPC) at 23° C. and pH=7 against polyacrylic acid sodium salt standard with the RID6a refractive index detector (Shimadzu) and comparative measurement with the MiniDawn light scattering detector (Wyatt), the last measurement as absolute measuring method making it possible to distinguish between unbranched and branched polyacids. Polyacrylic acid sodium salt standards (PSS) were used for calibrating the refractive index detector. The measured values were converted to free polyacrylic acid using the factor 0.766.

The samples were measured here as 0.05% aqueous solutions in the solvent, a 0.9% by weight aqueous sodium nitrate solution, to which 200 ppm of sodium azide are also added. The solutions were adjusted to pH=7 by addition of sodium hydroxide.

A column combination of Hema3000, HemaBio1000 and HemaBio40 (PSS) was used to measure maximum molecular weights of up to 670 000 g/mol. A column combination of Suprema1000, Hema3000 and HemaBio1000 (PSS) was used with maximum molecular weights of up to 1 100 000 g/mol.

PREPARATION EXAMPLE 1

4-Arm Star Polyacrylic Acid (PAA-4)

5.0 g (11.1 mmol) of 1,2,4,5-tetrakis(bromomethyl)benzene, 18.2 g (211 mmol) of methyl acrylate, 0.27 g of copper powder, 1.56 g of copper(II) triflate and 1.46 g of N,N,N',N", N"-pentamethyldiethylenetriamine are mixed together under a nitrogen atmosphere. The dark mixture is heated at 80° C. with stirring for 17 hours. A $^1$H NMR spectrum afterwards shows complete reaction of the benzyl bromide groups (disappearance of the signal at 4.6 ppm), so that equal growth of the four arms can be assumed.

200 g of methyl acrylate are added and the mixture is heated at 80° C. for a further 20 hours. In the course of this, the reaction mixture becomes viscous. A monomer conversion of approximately 98% is established by means of a $^1$H NMR spectrum.

The polymerizate is dissolved in 2 liters of methylene chloride and successively extracted with 2M hydrochloric acid and water. The final aqueous wash has a pH of 5.

Saponification is carried out by treating the organic solution with one part by volume of 4M aqueous potassium hydroxide solution and heating at 40° C. with vigorous stirring. The conversion is monitored by $^1$H NMR spectroscopy and is complete after 48 hours. The aqueous phase is separated and treated several times with an acidic ion-exchange material.

The concentration is adjusted to 40% by weight by concentrating under vacuum and monitoring by means of titration with lithium hydroxide. The potassium content is less than 100 ppm by atomic absorption spectroscopy.

Yield: 424 g (corresponds to a polymer yield of 92%).

The following values were established using a refractive index detector against a linear polyacrylic acid sodium salt standard (PAS) or with a light scattering detector (LS):
Mw=133 000 (LS) or 88 000 (PAS)
Mn=78 000 (LS) or 44 000 (PAS)
Mw/Mn=1.7 (LS) or 2.0 (PAS).

PREPARATION EXAMPLE 2

6-Arm Star Polyacrylic Acid (PAA-6)

1.0 g of hexakis(bromomethyl)benzene with 180 mg of copper powder, 1 020 mg of copper(II) triflate, 960 mg of N,N,N',N'',N''-pentamethyldiethylenetriamine and 93.0 g of methyl acrylate are weighed out successively into a flask under a nitrogen atmosphere. The mixture is heated at 80° C. with stirring. After a reaction time of five days, the dark contents of the flask are very viscous. A conversion of >90% is established using $^1$H NMR spectroscopy.

The batch is dissolved in 2 liters of methylene chloride and successively extracted with 2M hydrochloric acid and water, so that the final aqueous wash has a pH of 5.

The organic phase is treated with one part by volume of 4M potassium hydroxide solution and heated at 40° C. for 3 days with vigorous stirring. The conversion of the saponification is afterwards complete according to $^1$H NMR. The aqueous phase is treated with an acidic ion-exchange material and brought to a concentration of 32% by weight by concentrating under vacuum (titration with LiOH). The potassium content is less than 100 ppm by atomic absorption spectroscopy.

Yield: 197 g (corresponds to a polymer yield of 81%).

The following values were established using a refractive index detector against a linear polyacrylic acid sodium salt standard (PAS) or with a light scattering detector (LS):
Mw=460 000 (LS) or 117 000 (PAS)
Mn=182 000 (LS) or 47 000 (PAS)
Mw/Mn=2.5 (LS) or 2.5 (PAS).

The GPC results confirm the star structure.

APPLICATION EXAMPLES

The polyacids according to the preparation examples were tested in the application for dental glass ionomer cements.

Bending strengths were determined using the ISO 4049 standard, in which, however, test specimens with a length of 12 mm were used. In each case, mean values from series of five test specimens with a relative error of approximately ±10% per measured value were determined. The procedure used to determine the compressive strengths of the set cements was that of the ISO 9917 standard. Surface hardnesses were determined analogously according to DIN 53456, the test specimens being stored in water at 36° C. up to the time of measurement.

The viscosities of the aqueous polyacid solutions were measured at 23° C. with a PK 100 viscometer from Haake.

Concentrations were determined by titration with lithium hydroxide in the presence of 1% by weight of lithium chloride.

The storage stability was established by storage of the polyacid solutions in glass flasks at ambient temperature (25° C.) and visual assessment of the samples at regular intervals of time. Several lots of each polyacid were stored, the analytical values of the various lots of each polyacid differing only slightly (deviations, maximum <10%).

The stated polyacids were spatulated with a standard glass ionomer powder based on a calcium strontium fluoroaluminosilicate glass (glass ionomer cement glass) (Diamond Carve Powder, Kemdent, England) with a powder/liquid ratio of 3.5/1 (parts by weight).

Two commercial (Aldrich) unbranched polyacrylic acids (PAA-1a and PAA-1b), with different average molar masses, were used as comparative example.

The results are summarized in table 1:

TABLE 1

| Polyacid | PAA-1a | PAA-1b | PAA-4 (according to the invention) | PAA-6 (according to the invention) |
|---|---|---|---|---|
| Concentration [%] (±1) | 42 | 35 | 44 | 40 |
| Mw (GPC-LS) | 60000 | 250000 | 133000 | 460000 |
| Mn (GPC-LS) | 12000 | 50000 | 78000 | 182000 |
| Viscosity [Pa · s] | 8.0 | 8.2 | 8.4 | 7.7 |
| Bending strength [MPa] | 42 | 45 | 47 | 44 |
| Storage stability as regards gelling | <6 months (3 of 5 lots) | <6 months (2 of 3 lots) | >24 months (all lots) | >24 months (all lots) |

In spite of clearly higher average molar masses and higher concentrations of the star polyacids, the bending strengths and the viscosities lie at the same level as in the reference substances (Comparison: PAA-4 with PAA-1a and PAA-6 with PAA-1b). However, the star acids also show a reliable storage stability over 24 months, while, of the unbranched reference acids, several lots were already irreversibly gelled within six months and were accordingly unusable.

The invention claimed is:

1. A dental material including:
   A. 1 to 60% by weight of polyacids, in which the polyacids used have at least one branching point in the polymer structure, are water-soluble and noncrosslinked and, with regard to the repeat units, comprise at least 80 mol % acrylic acid segments, the term "branching point" being understood as meaning a position in the polymer backbone from which, covalently bonded, at least two polymer residues start out, these comprising at least three repeat units;
   B. 35 to 80% by weight of fillers;
   C. 0 to 20% by weight of additives and auxiliaries;
   D. 5 to 40% by weight of water.

2. The dental material of claim 1, wherein polyacids, together with at least one salt of at least one polyacid, being used as component (A), in which the polyacids used have at least one branching point in the polymer structure, are water-soluble and noncrosslinked and, with regard to the repeat units, comprise at least 80 mol % acrylic acid segments.

3. A dental material including:
   A. 1 to 60% by weight of polyacids, in which the polyacids used have at least one branching point in the polymer structure, are water-soluble and noncrosslinked and, with regard to the repeat units, comprise at least 80 mol % acrylic acid segments, the term "branching point" being understood as meaning a position in the polymer backbone from which, covalently bonded, at least two polymer residues start out, these comprising at least three repeat units;

C. 0 to 20% by weight of additives and auxiliaries;
D. 10 to 40% by weight of water;
E. 30 to 80% by weight of zinc oxide.

4. The dental material as claimed in claim 3, wherein polyacids, together with at least one salt of at least one polyacid, being used as component (A), in which the polyacids used have at least one branching point in the polymer structure, are water-soluble and noncrosslinked and, with regard to the repeat units, comprise at least 80 mol % acrylic acid segments.

5. A dental material including:
A. 1 to 76% by weight of polyacids, in which the polyacids used have at least one branching point in the polymer structure, are water-soluble and noncrosslinked and, with regard to the repeat units, comprise at least 80 mol % acrylic acid segments, the term "branching point" being understood as meaning a position in the polymer backbone from which, covalently bonded, at least two polymer residues start out, these comprising at least three repeat units;
D. 5 to 40% by weight of water;
F. 8.9 to 70% by weight of one or more radically polymerizable monomers;
G. 10 to 90% by weight of fillers;
H. 0.1 to 5% by weight of initiators and optionally activators;
I. 0 to 30% by weight of additives, optionally pigments, thixotropic auxiliaries, plasticizers.

6. The dental material as claimed in claim 5, wherein polyacids, together with at least one salt of at least one polyacid, being used as component (A), in which the polyacids used have at least one branching point in the polymer structure, are water-soluble and noncrosslinked and, with regard to the repeat units, comprise at least 80 mol % acrylic acid segments.

7. A container including the dental material as claimed in claim 1.

8. A container including the dental material as claimed in claim 3.

9. A container including the dental material as claimed in claim 5.

10. A material comprising:
at least one polyacid or at least one polyacid together with at least one salt of at least one polyacid, the polyacids employed having at least one branching point in the polymer structure, being water-soluble and non-crosslinked and, with regard to the repeat units, comprising at least 80 mol % acrylic acid segments, the term "branching point" being understood as meaning a position in the polymer backbone from which, covalently bonded, at least two polymer residues start out, these comprising at least three repeat units; and
one or more radically polymerizable monomers,
wherein the material is a curable dental material.

11. The material as claimed in claim 10, wherein the polyacids comprise star polymers or comb polymers.

12. The material of claim 10, wherein the polyacids are copolymers in which the proportion of the comonomers amounts to 0.1 to 20 mol %.

13. A container including the material as claimed in claim 10.

14. The material of claim 11, wherein the polyacids are copolymers in which the proportion of the comonomers amounts to 0.1 to 20 mol %.

15. A material comprising:
at least one polyacid or at least one polyacid together with at least one salt of at least one polyacid, the polyacids employed having at least one branching point in the polymer structure, being water-soluble and non-crosslinked and, with regard to die repeat units, comprising at least 80 mol % acrylic acid segments, the term "branching point" being understood as meaning a position in the polymer backbone from which, covalently bonded, at least two polymer residues start out, these comprising at least three repeat units; and
one or more reactive fillers,
wherein the material is a curable dental material in which the one or more reactive fillers can react with the at least one polyacid or at least one polyacid together with at least one salt of at least one polyacid.

16. The material as claimed in claim 15, wherein the polyacids comprise star polymers or comb polymers.

17. The material of claim 15, wherein the polyacids are copolymers in which the proportion of the comonomers amounts to 0.1 to 20 mol %.

18. A container including the material as claimed in claim 15.

19. The material of claim 16, wherein the polyacids are copolymers in which the proportion of the comonomers amounts to 0.1 to 20 mol %.

* * * * *

UNITED STATES PATENT AND TRADEMARK OFFICE
CERTIFICATE OF CORRECTION

PATENT NO. : 7,456,232 B2
APPLICATION NO. : 10/432946
DATED : November 25, 2008
INVENTOR(S) : Mikulla et al.

It is certified that error appears in the above-identified patent and that said Letters Patent is hereby corrected as shown below:

On the Title Pg Item (54) in the Title, delete, "USE OF BRANCHED POLYACIDS IN DENTAL COMPOUNDS" and insert --USE OF BRANCHED POLYACIDS IN DENTAL MATERIALS--;

In column 1, line 1, delete "USE OF BRANCHED POLYACIDS IN DENTAL COMPOUNDS" and insert --USE OF BRANCHED POLYACIDS IN DENTAL MATERIALS--;

In column 14, line 24, delete "die" and insert --the--.

Signed and Sealed this

Twenty-third Day of June, 2009

JOHN DOLL
*Acting Director of the United States Patent and Trademark Office*